US010614913B2

United States Patent
Sethumadhavan et al.

(10) Patent No.: US 10,614,913 B2
(45) Date of Patent: Apr. 7, 2020

(54) SYSTEMS AND METHODS FOR CODING HEALTH RECORDS USING WEIGHTED BELIEF NETWORKS

(71) Applicant: Apixio, Inc., San Mateo, CA (US)

(72) Inventors: Vishnuvyas Sethumadhavan, Mountain View, CA (US); Jose Cruz Toledo, Redwood City, CA (US)

(73) Assignee: APIXIO, INC., San Mateo, CA (US)

( * ) Notice: Subject to any disclaimer, the term of this patent is extended or adjusted under 35 U.S.C. 154(b) by 208 days.

(21) Appl. No.: 15/709,465

(22) Filed: Sep. 19, 2017

(65) Prior Publication Data
US 2018/0075192 A1    Mar. 15, 2018

Related U.S. Application Data

(63) Continuation-in-part of application No. 13/223,228, filed on Aug. 31, 2011, now Pat. No. 10,176,541, and
(Continued)

(51) Int. Cl.
*G16H 10/60*    (2018.01)
*G06K 9/62*    (2006.01)
(Continued)

(52) U.S. Cl.
CPC ............. *G16H 10/60* (2018.01); *G06F 16/20* (2019.01); *G06F 16/21* (2019.01);
(Continued)

(58) Field of Classification Search
CPC ......... G16H 10/60; G06F 16/21; G06F 16/20; G06K 9/6267; G06K 9/00442;
(Continued)

(56) References Cited

U.S. PATENT DOCUMENTS 6,336,108 B1 *  1/2002  Thiesson .............. G06K 9/6296
                                                        706/20
7,321,861 B1    1/2008  Oon
                (Continued)

FOREIGN PATENT DOCUMENTS

JP           4471736 B2      3/2010
JP       2010-134946 A       6/2010
                (Continued)

OTHER PUBLICATIONS

Korean Intellectual Property Office, ISA, "International Search Report and Written Opinion" in PCT Application No. PCT/US2012/053182, dated Mar. 18, 2013, 12 pages.
(Continued)

*Primary Examiner* — Huan V Doan
(74) *Attorney, Agent, or Firm* — Kang S. Lim

(57) ABSTRACT

Systems and methods to code medical records using weighted belief networks are provided. Medical records are received, and may be subjected to pre-processing which includes deduplication of records, indexing the records, meta-tagging the records, and annotating the records. An entity extractor then generates entity dictionaries from public sources. A network creator generates a belief network based on medical relationships. An annotation aligner receives normalized annotations of historical medical records, and a network weighter assigns probability values to the belief network using the normalized annotations to generated a weighted belief network. A health care code classifier utilizes the weighted belief network to classify the medical records by comparing entities within the medical records.

20 Claims, 12 Drawing Sheets

Related U.S. Application Data a continuation-in-part of application No. 13/747,336, filed on Jan. 22, 2013, now abandoned.

(60) Provisional application No. 62/397,663, filed on Sep. 21, 2016, provisional application No. 61/379,228, filed on Sep. 1, 2010, provisional application No. 61/590,330, filed on Jan. 24, 2012.

(51) Int. Cl.
| | |
|---|---|
| *G06K 9/00* | (2006.01) |
| *G06N 7/00* | (2006.01) |
| *G06F 16/20* | (2019.01) |
| *G06F 16/21* | (2019.01) |
| *G06Q 40/08* | (2012.01) |
| *G06Q 30/04* | (2012.01) |

(52) U.S. Cl.
CPC ....... *G06K 9/00442* (2013.01); *G06K 9/6267* (2013.01); *G06K 9/6296* (2013.01); *G06N 7/005* (2013.01); *G06Q 30/04* (2013.01); *G06Q 40/08* (2013.01); *G06K 2209/01* (2013.01)

(58) Field of Classification Search
CPC .. G06K 9/6296; G06K 2209/01; G06Q 30/04; G06Q 40/08; G06N 7/005
See application file for complete search history.

(56) References Cited

U.S. PATENT DOCUMENTS

| | | | |
|---|---|---|---|
| 2003/0120640 A1* | 6/2003 | Ohta | G06F 16/248 |
| 2004/0220895 A1* | 11/2004 | Carus | G06Q 50/22 |
| 2005/0138017 A1 | 6/2005 | Keen et al. | |
| 2005/0192792 A1* | 9/2005 | Carus | G06F 17/2735 |
| | | | 704/2 |
| 2006/0036619 A1 | 2/2006 | Fuerst et al. | |
| 2006/0047669 A1 | 3/2006 | Durrence et al. | |
| 2006/0053098 A1* | 3/2006 | Gardner | G06F 16/367 |
| 2006/0129435 A1 | 6/2006 | Smitherman et al. | |
| 2006/0241978 A1 | 10/2006 | Yoshii | |
| 2007/0016450 A1 | 1/2007 | Bhora et al. | |
| 2007/0088559 A1* | 4/2007 | Kim | G06F 19/3418 |
| | | | 715/705 |
| 2008/0091633 A1 | 4/2008 | Rappaport et al. | |
| 2008/0195570 A1* | 8/2008 | Alsafadi | G16B 50/00 |
| | | | 706/53 |
| 2008/0263048 A1 | 10/2008 | Wise | |
| 2008/0270120 A1* | 10/2008 | Pestian | G06F 17/2785 |
| | | | 704/9 |
| 2008/0270340 A1 | 10/2008 | Abrams et al. | |
| 2009/0024615 A1 | 1/2009 | Pedro et al. | |
| 2009/0070103 A1* | 3/2009 | Beggelman | G06F 17/27 |
| | | | 704/9 |
| 2009/0076839 A1* | 3/2009 | Abraham-Fuchs | G06Q 10/10 |
| | | | 705/2 |
| 2009/0112882 A1 | 4/2009 | Maresh et al. | |
| 2009/0136102 A1 | 5/2009 | Kimpe et al. | |
| 2009/0271221 A1 | 10/2009 | Aridi et al. | |
| 2010/0131482 A1 | 5/2010 | Linthicum et al. | |
| 2010/0179827 A1 | 7/2010 | McCallie, Jr. et al. | |
| 2010/0185496 A1* | 7/2010 | Hahn | G06Q 30/00 |
| | | | 705/7.33 |
| 2011/0004588 A1* | 1/2011 | Leitersdorf | G06F 16/951 |
| | | | 707/711 |
| 2011/0196702 A1 | 8/2011 | Hani et al. | |

FOREIGN PATENT DOCUMENTS

| | | |
|---|---|---|
| KR | 10-0750071 B1 | 8/2007 |
| KR | 10-2009-0050881 | 5/2009 |

OTHER PUBLICATIONS

Korean Intellectual Property Office, ISA, "International Search Report and Written Opinion" in PCT Application No. PCT/US2013/022813, dated May 30, 2013, 10 pages.

* cited by examiner

SYSTEMS AND METHODS FOR CODING HEALTH RECORDS USING WEIGHTED BELIEF NETWORKS

CROSS REFERENCE TO RELATED APPLICATION

This non-provisional application claims the benefit of provisional application No. 62/397,663, filed Sep. 21, 2016, of the same title, which application is incorporated herein in its entirety by this reference.

This also is a continuation-in-part application which claims the benefit of application Ser. No. 13/223,228 filed on Aug. 31, 2011, entitled "Medical Information Navigation Engine (MINE) System", which application claims priority to U.S. Provisional Application No. 61/379,228 filed on Sep. 1, 2010, of the same title, both applications are incorporated herein in their entirety by this reference.

Additionally, this continuation-in-part application claims the benefit of application Ser. No. 13/747,336 filed on Jan. 22, 2013, entitled "Knowledge Extraction and Exchange Method and Apparatus", which application claims priority to U.S. Provisional Application No. 61/590,330 filed on Jan. 24, 2012, of the same title, both applications are incorporated herein in their entirety by this reference.

BACKGROUND

The present invention relates generally to the ability to code medical documents based upon weighted belief networks. In particular, the systems and methods disclosed herein relate to the ability to apply acceptable Medicare or other insurance codes to assist in reimbursement and billing of medical services provided. Unlike manual coding, which is currently employed, the present systems provide more accurate, consistent, and rapid identification of actionable codes within a medical record.

Despite rapid growth of innovation in other fields in recent decades, the world of medical information, including patient medical records, billing, referrals, and a host of other information, has enjoyed little to no useful consolidation, reliability, or ease-of-access, leaving medical professionals, hospitals, clinics, and even insurance companies with many issues, such as unreliability of medical information, uncertainty of diagnosis, lack of standard, and a slew of other related problems.

One of the challenges facing those in the medical or related areas is the number of sources of information, the great amount of information from each source, maintenance of data in a HIPAA compliant manner, and consolidation of such information in a manner that renders it meaningful and useful to those in the field in addition to patients. Obviously, this has contributed to increased medical costs and is perhaps largely attributed to the field suffering from an organized solution to better aid the medical professionals, to better aid those requiring more reliable patient history and those requiring more control and access over such information.

The concept of "big data" is already well established in the field of information technology. Big data is a collection of tools, techniques and methodologies used when data sets are large and complex that it becomes difficult or impossible to store, query, analyze or process using current database management and data warehousing tools or traditional data processing applications. The challenges of handling big data include capture, curation, storage, search, sharing, analysis and visualization. The trend to larger data sets is due to the proliferation of data capture devices and the ease of capturing and entering data from a wide variety of sources.

Due to the intrinsic issues prevalent with medical information—where very large amounts of clinical and administrative information are generated and stored as unstructured text and scanned documents, big data platforms and analysis is all but unheard of Additionally, even when the data is readily machine readable, often the ability to properly analyze complex medical terms and conditions is limited to specialized individuals who must manually review each medical document individually. Such methods of document review are slow, error prone, costly, and subject to different outcomes based upon the reviewer. In the context of analyzing a record for a Medicare reimbursable event (a process known as coding), this can result in a significant loss of revenue and possibly reduced treatment efficacy.

It is therefore apparent that an urgent need exists for tools that allow for the analysis of medical information in order to code medical records automatically and efficiently. Specifically, the utilization of weighted belief networks may enable rapid, accurate and automated coding of medical records.

SUMMARY

To achieve the foregoing and in accordance with the present invention, systems and methods for coding medical records based upon weighted belief networks are provided. Such systems and methods enable the rapid and accurate application of Medicare (or other desired) codes to a medical record without the need for costly manual review.

In some embodiments, medical records are received, and may be subjected to pre-processing which includes deduplication of records, indexing the records, meta-tagging the records, and annotating the records. An entity extractor then generates entity dictionaries from public sources. A network creator generates a belief network based on medical relationships. An annotation aligner receives normalized annotations of historical medical records, and a network weighter assigns probability values to the belief network using the normalized annotations to generate a weighted belief network. A health care code classifier utilizes the weighted belief network to classify the medical records by comparing entities within the medical records.

In some embodiments, the belief network is a Bayesian network. The belief network may be a cyclic directed graph with nodes of random variables and relationships between the nodes codify parent/child relationships. Each of the random variables may include a domain, and the belief network includes a set of conditional probability distributions for each variable X given by: $P(X|parents(X))$. In some cases, the belief network is a triple data structure comprising a subject-predicate-object.

The medical relationships used to generate the belief network is a Web Ontology Language (OWL) and Resource Description Framework (RDF) ontologies. The classified documents may be used to output to a human coder for further verification or review.

Note that the various features of the present invention described above may be practiced alone or in combination. These and other features of the present invention will be described in more detail below in the detailed description of the invention and in conjunction with the following figures.

BRIEF DESCRIPTION OF THE DRAWINGS

In order that the present invention may be more clearly ascertained, some embodiments will now be described, by way of example, with reference to the accompanying drawings, in which.

DETAILED DESCRIPTION

Figure 1:
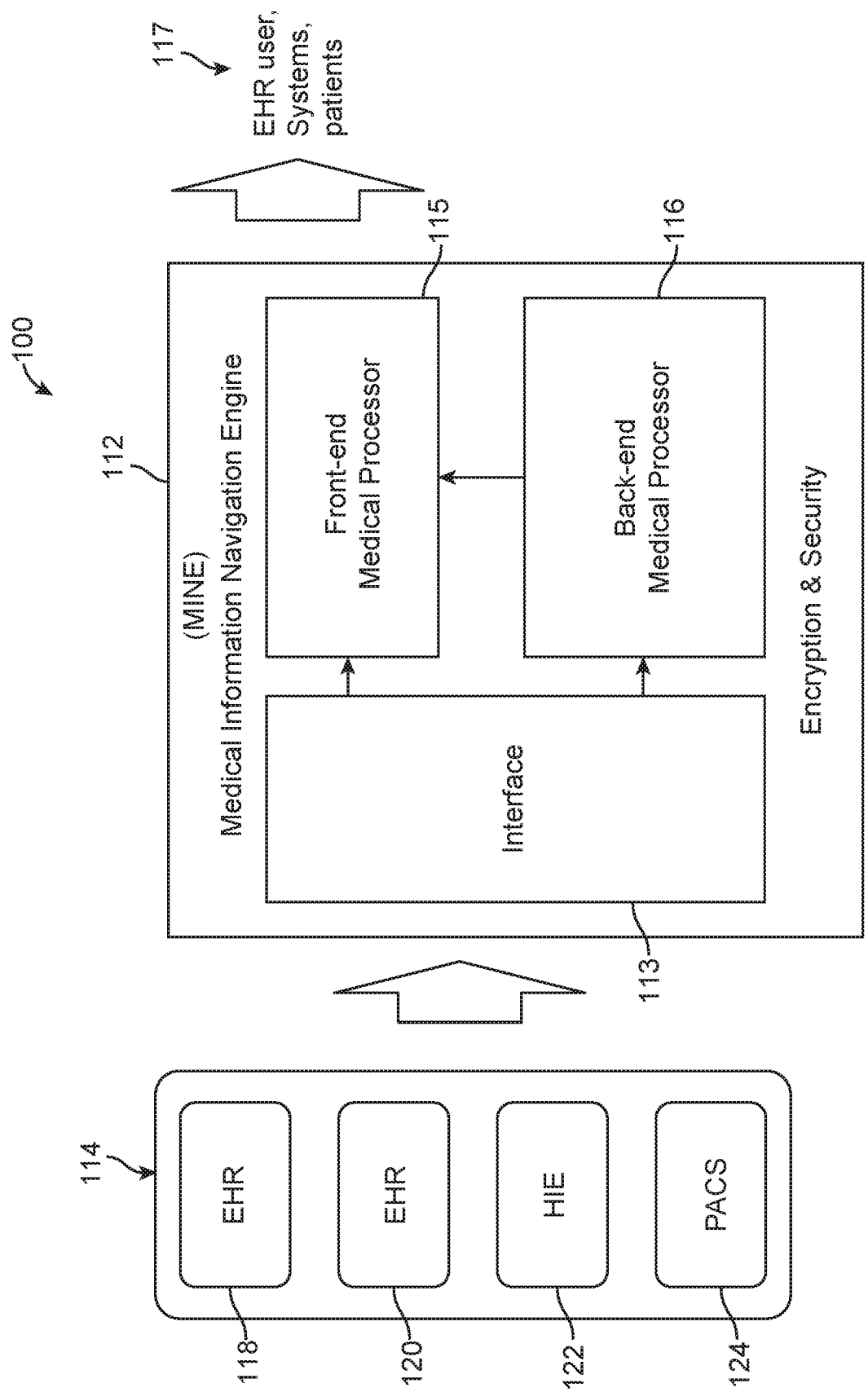
FIG. 1 shows a medical information system, in accordance with some embodiments.

The present invention will now be described in detail with reference to several embodiments thereof as illustrated in the accompanying drawings. In the following description, numerous specific details are set forth in order to provide a thorough understanding of embodiments of the present invention. It will be apparent, however, to one skilled in the art, that embodiments may be practiced without some or all of these specific details. In other instances, well known process steps and/or structures have not been described in detail in order to not unnecessarily obscure the present invention. The features and advantages of embodiments may be better understood with reference to the drawings and discussions that follow.

Aspects, features and advantages of exemplary embodiments of the present invention will become better understood with regard to the following description in connection with the accompanying drawing(s). It should be apparent to those skilled in the art that the described embodiments of the present invention provided herein are illustrative only and not limiting, having been presented by way of example only. All features disclosed in this description may be replaced by alternative features serving the same or similar purpose, unless expressly stated otherwise. Therefore, numerous other embodiments of the modifications thereof are contemplated as falling within the scope of the present invention as defined herein and equivalents thereto. Hence, use of absolute and/or sequential terms, such as, for example, "will," "will not," "shall," "shall not," "must," "must not," "first," "initially," "next," "subsequently," "before," "after," "lastly," and "finally," are not meant to limit the scope of the present invention as the embodiments disclosed herein are merely exemplary.

The present invention relates to the automated coding of medical records using belief networks systems and methods. More particularly, the present disclosure focuses on the ability to probabilistically classify code-able conditions within the medical records by weighting the belief network to reflect statistical probability that the evidence for the condition actually indicates its existence.

Within the field of medical record big-data, such ability to make classifications within the records enables the efficient and rapid coding of the data for Medicare reimbursement. This reduces the need for resource heavy manual review, and greater record throughput. While this disclosure will focus almost exclusively upon the coding of medical records, it should be understood that these systems and methods may be applied to any situation where extensive free-form records require analysis for a classification or condition with a high degree of accuracy and efficiency. Thus while the medical field is provided by way of example, it should be readily understood that these techniques may be applied to the legal field, business operations, research, archiving, or virtually any applicable field.

For example, in some embodiments the disclosed system is a flexible, highly-scalable big-data enterprise system that understands concepts, and associations and relationships between the concepts from unstructured text using machine learning and nlp (natural language processing) techniques. The system is completely language independent and domain independent as it extracts the concepts and relationships directly from its input text. Thus, the code generation using belief networks can be constructed and utilized across multilingual documents and can also be utilized across multiple domains (e.g.: Healthcare, Legal, etc.). In fact, even within the field of healthcare, the data does not all need to be medical in nature. The data can be of variety of types including administrative, workflow, process, inventory, lifestyle, technology, etc. As such, it is considered that any situation where big data analysis is desirable may be within the scope of this disclosure. Again, note that the discussion contained herein will primarily be centered on medical information for the sake of clarity and specialized examples.

The following description of some embodiments will be provided in relation to numerous subsections. The use of subsections, with headings, is intended to provide greater clarity and structure to the present invention. In no way are the subsections intended to limit or constrain the disclosure contained therein. Thus, disclosures in any one section are intended to apply to all other sections, as is applicable.

I. Medical Systems

To facilitate the discussion, FIG. 1 illustrates a medical system 100, in accordance with an embodiment of the invention. The system 100 is shown to include medical source 114, a medical information navigation engine (MINE) 112, and medical information consumers (also referred to herein as "output" or "medical output") 117. The medical source 114 are shown to include an electronic health record (EHR) 118, EHR 120, health information exchange (HIE) 122, and a picture archiving and communication system (PACS) 124. The MINE 112 is shown to include interface 113, a back-end medical processor 116, and a front-end medical processor 115.

The MINE 112 disclosed herein, is capable of receiving medical information data, and de-duplicating, converting the information into machine readable data, indexing and tagging the data in order to allow for downstream analysis. "Medical information", as used herein, refers to any health-related information, including but not limited to patient medical records, patient entered information, care team entered information, healthcare device generated information, and billing information.

The source 114 generally provides various medical information to the MINE 112. For example, the EHRs 118 and 120 each may provide information such as medical records and billing, the HIE 122 may provide information such as medical records, and the PACS 124 may provide information such as diagnostic imaging and reports.

The medical information consumers 117, which may be made of a host of entities or individuals, such as patients, clinics, medical institutions, health organization, and any other medical-related party, use information that is provided by the processor 115 of MINE 112 and that can, by way of example, consist of patients, medical systems, medical organization administrators, medical researchers, and/or EHR users. For example, user-customized processed medical information (indexed and tagged) is provided by the processor 115 to a number of users within the medical information consumers 117. In this case, the processor 115 generates user-customized processed medical information to a plurality of users, with at least a portion of the user-customize processed medical information being provided to each of the users based on the relevancy of the portion being provided of each user's specific function or role and each user's associated security privileges.

The processor 116, in some embodiments, indexes identifies, maps, and consolidates medical information, received from the interface 113, and tags this information, and determines to reconcile the tagged information. In some methods and embodiments, information that is extracted from images via optical character recognition (OCR). The extracted data is then tagged to enhance recall of search queries. Indexing, at least in part, processes document and converts them into formats that allows for quick searching across a large collection of documents. The records, once processed, are then subject to automated classification utilizing belief networks, which will be discussed in considerable detail below, and additional downstream analytics.

The information in the MINE 112 is encrypted and secure to ensure privacy of sensitive medical information. Likewise, any final event streams provided to downstream applications may be encrypted or otherwise anonomized in order to comport to HIPAA and other privacy regulations.

It is understood that the sources 114 of FIG. 1 includes merely some examples of the sources that communicate with the MINE 112 and that other sources, known to those in the field, are contemplated. Similarly, the output 117 may be used by those or entities not discussed herein but that are contemplated and within the scope and spirit of the invention.

The interface 113 serves to receive information that is in various forms, such as but not limited to text, html, CCD, CCR, HL7 and any other type or formatted information. The interface 113 then provides to the processors 115 and 116 information, as needed.

The processor 116 receives some of the medical information that the interface 113 processes and performs certain tasks to process it, such as indexing, semantic meta-tagging, and reconciliation. Indexing takes processed documents and converts them into formats that make it easy to quickly search across a large collection of documents. Semantic meta-tagging embeds information into the medical information that is relevant thereto and that can be later used to search for certain information for the purpose of reconciliation and search, among many others.

One aspect of consolidation, reconciliation and de-duplication, generally refers to removing of redundant patient medical records, such as, multiple records for the same individual appearing as though the records are for different individuals or multiple data elements that are recorded similarly but slightly differently in the different sources. In this case, the processor 116 recognizes that the records belong to a single individual or are the same data and just recorded differently and automatically consolidates them. The patient or a user of the system 100 may also manually perform reconciliation. The processor 116 advantageously determines whether or not reconciliation is performed.

The processor 116 outputs the indexed, tagged and reconciled information to the processor 115. The foregoing tasks are a generalization, and further details of each are provided below.

The processor 115 performs certain tasks on the information provided by the interface 113 and the processor 116, which include query, search, presentation, and quality checking, and ultimately downstream analysis, such as classification of codes using belief networks, coder sorting, or the like. The output of the processor 115 may be an indexed document, coded document, or other output 117.

The MINE 112, through the processor 115, in some embodiments and methods, invites members of a medical care team to join it thereby allowing distributed user-organized care teams.

Querying, as performed by the processor 115, is the ability to receive, as input, a free text query, from a user, (e.g., a query without any restrictions on the structure)—and converting the free text query into commands to a medical search engine, such as Medical Lexical Search Engine and the MATRIX (Medical Application Terminology Relationship IndeX) Concept Search Engine, using a sophisticated query processing engine optimized to work with medical queries. The results of the search engine are sent to the presentation display planner—which decides the most relevant presentation given the user's organization and role (e.g., the provider, search query program, a healthcare administrator, a study administrator, and the patient). The presentation discussed below, receives such information. In some embodiments and methods, the medical information or user information is processed to suggest relevant queries.

Search, as performed by the processor 115, is built around the concept of Zero-Click Relevance—or the ability to get to all the relevant information an actor in the healthcare system requires by typing in just a single query. The search engine, within the processor 115, performing the search comprises an indexing and searching, as will become apparent shortly. Optionally, search results may be securely embedded into third party programs. In some embodiments, searching involves determining presenting (also referred to herein as "providing") access to specific relevant data based on a search query, the patient, and the user's specific function and/or role and security privileges. A user may be within the output 117 and security privileges are either determined by the MINE 112 or by the patient or both. The information that is uploaded to the MINE 112 by users, such as in output 114 (in some embodiments) is searched by the processor 115. The uploaded information may include information such as but not limited to status posts, records, and images. Such user-uploaded information is routed automatically to the output 117, as needed.

Some aspects of the search are now discussed relevant to an example. Assuming, by way of example, that Dr. Smith, an internal medicine physician, sees a new patient, Joan Sample, who presents with a complaint of chest pain. Joan has brought several continuity-of-care documents (CCDs) and a 600-page pdf file representing of her medical chart. She has seen a cardiologist who uses NextGen's electronic medical record (EMR) and a gastroenterologist who uses eMD's EMR and she has recently visited a local emergency room. Dr. Smith uses the search of the various methods and embodiments of the invention to efficiently assemble the relevant information he needs. Dr. Smith selects Joan Sample as the patient and enters the clinical context "chest pain" in the search bar of a screen presented by the MINE 112. He is presented with relevant lab results, such as CKMB, troponin, and amylase, relevant diagnostic results, such as prior electrocardiograms (EKGs) and the most recent chest computed tomography (CT) scan; and all progress notes and consult reports in which concepts relevant to chest pain, like "GERD" and "cardiac stress test", are mentioned. Two distinct types of searches are combined, in accordance with a method and embodiment of the invention, to retrieve information medically relevant to Joan's complaint: 1) Lexical search, where text in the patient record is searched for occurrences of the search term, its variants and synonyms; and 2) Medical concept search, where data that is medically related to the search term is retrieved. Medical concept search finds relevant structured data with standardized codes, such as lab results, and text results, such as progress notes, which include terms medically related to the search term.

In Joan's case, a search for "chest pain" returns a CKMB lab result and a reference to the most recent chest CT scan. Accordingly and advantageously, the Lexical and Medical concept search solves Dr. Smith's information overload problem by returning information in the chart most relevant to determining the etiology of Joan's chest pain complaint. Further, in some embodiments, the presentation, discussed shortly, presents a united view of Joan's history by reconciling and de-duplicating data from multiple sources that may be coded and described differently. Redundant data is automatically reconciled even if it is described differently by differently sources.

Presentation, as performed by the processor 115, is displaying health information to the requesting user in a way that reduces the number of clicks and maximizes the amount of meaningful information delivered based on the interpreting the intent of the user query.

Quality checking, as performed by the processor 115, is checking of the quality of medical information provided by various sources, i.e. source 114, by the patients, structured data, and unstructured data, in a Wiki-like mannered setting whereby the users can help maintain and improve the quality of information displayed. The foregoing tasks, performed by the processor 115, are further described in detail below. Additionally, the users or patients may make comments regarding medical information, in a Wiki-like manner.

In summary, the MINE 112 transacts medical information including the interface 113 receiving medical information from a number of medical sources (such as within the source 114) for processing, identifying, mapping, consolidating, and classifying by the medical processor 116, providing access to specific relevant data, based on a user's security privileges, within the identified, mapped, and consolidated medical information, based on user-specific functions or roles, performed by the processor 115, and generating user-customized processed medical information to a number of users, such as within the output 117, with at least a portion of the user-customized processed medical information being provided to each of the users based on its relevancy to each user's specific function or role and each user's associated security privileges.

Figure 2:
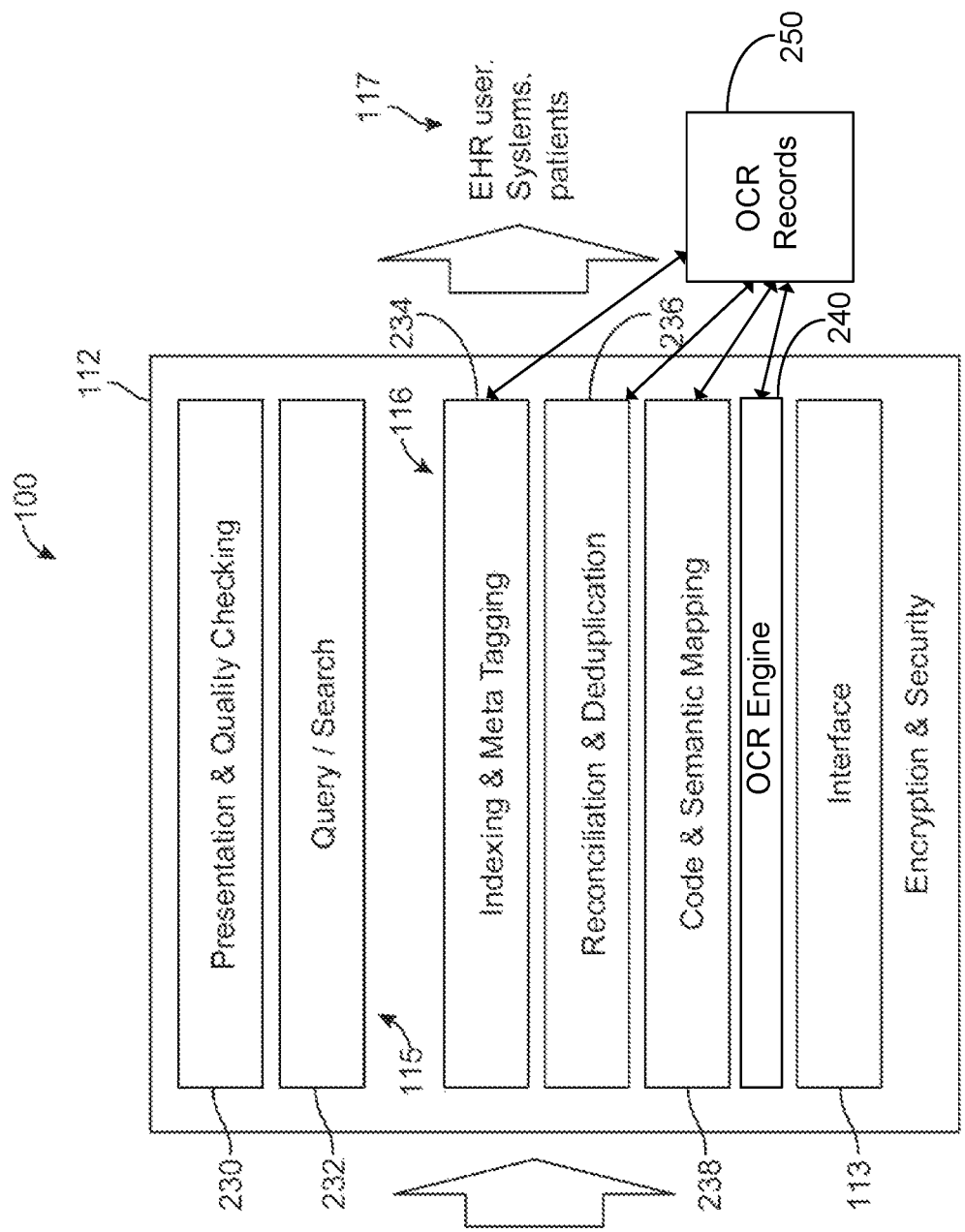
FIG. 2 shows further details of the system, particularly the Medical Information Navigation Engine (MINE) thereof, in accordance with some embodiments.
Figure 2:
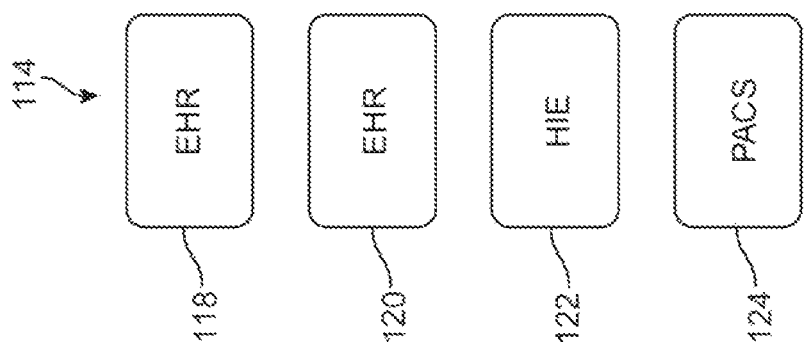

FIG. 2 shows further details of the system 100, particularly the MINE 112 thereof. That is, the processor 116 is shown to include an indexing and meta tagging module 234, which includes an indexing module and a meta tagging module (both of which are not shown in FIG. 2 in the interest of clarity), which may be a module, as shown in FIG. 2 or two physically separate modules. The processor 116 is further shown to include a reconciliation and de-duplication module 236, which also can be broken out into two modules, a reconciliation module and a de-duplication module, and a code and semantic mapping module 238, which also may be a single module or multiple modules. The output of the tagging module, reconciliation and semantic mapping is processed data for consumption by the HER user or other downstream systems 117.

Prior to indexing and reconciling the data, an OCR engine 240 may consume free-form electronic medical records and convert them into machine readable data sources. The output of the OCR engine 240 are the OCR records 250, which are consumable by the modules 234, 236 and 238.

The foregoing modules may be software programs, executed by a computer or computing engine of suitable sorts, or may be implemented in hardware.

Figure 3:
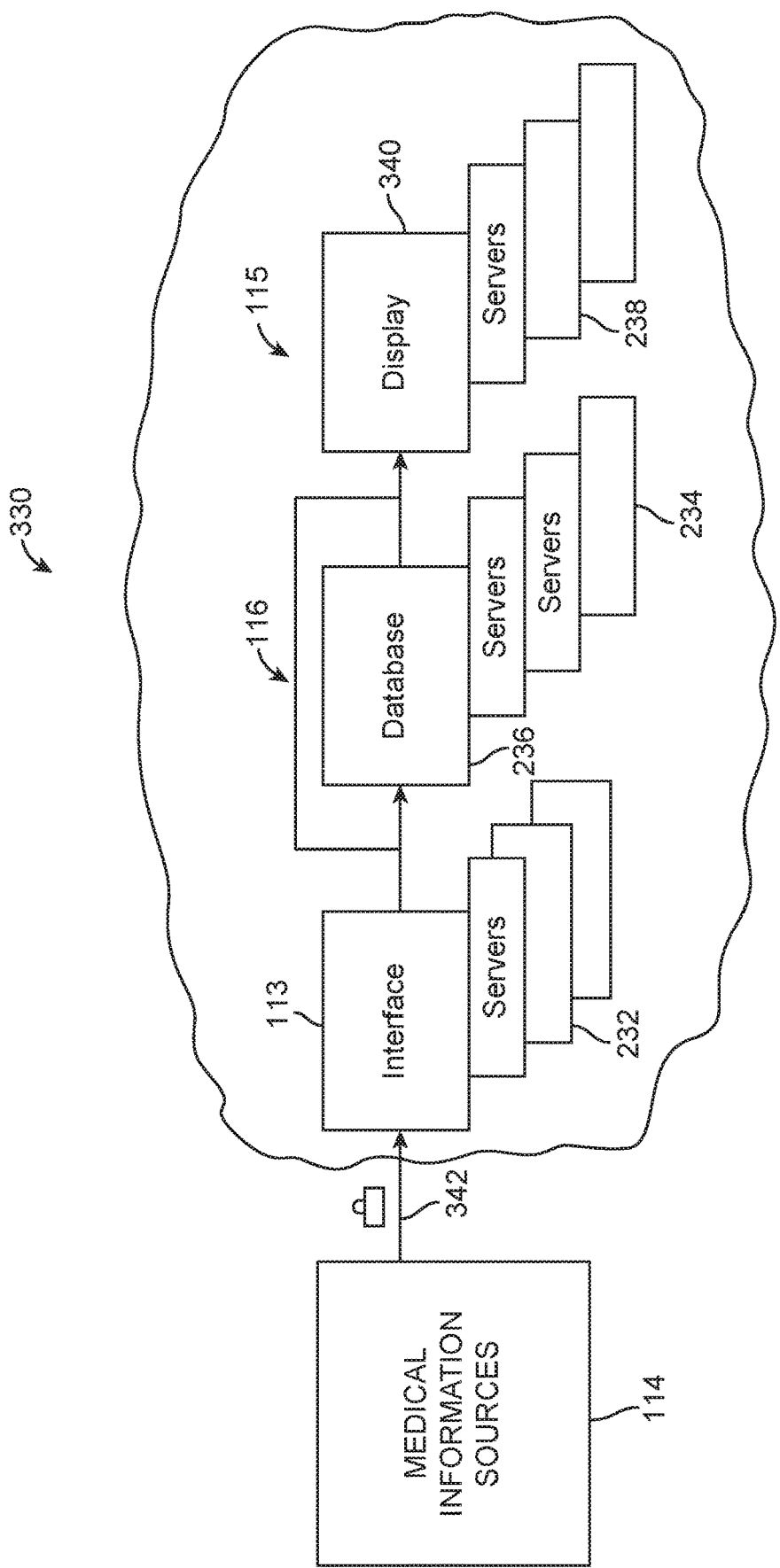
FIG. 3 shows an exemplary embodiment implementing the system using various devices, in accordance with some embodiments.

FIG. 3 shows an exemplary embodiment implementing the system 100 using various devices. That is, the medical system 330 is analogous to the system 100 and is shown to include the sources 114 coupled to communicate, securely, through the secure communication link 342, to the interface 113. The link 342 may be any suitable communication channel allowing information, of various formats and types, to be transferred to the interface 113 in a secure and encrypted fashion. Exemplary communication channels of which the link 342 is made include the Internet, VPN connections over the Internet, private dedicated digital lines such as T1, T3, E1, E3, SONET, and other fiber optic formats.

The interface 113, in some embodiments, is a software program that executes on one or more servers 232, which can be a server of any kind of suitable computing engine, such as personal computer (PC). The servers 232 receive secure information through the link 342 from the sources 114. The processor 116, in some embodiments, includes the module 236 and one or more servers 234, which may be any suitable computing engine, similar to the servers 232, including but not limited to PCs or servers.

The module 236 and servers 234 perform the tasks discussed above relative to the processor 116 and the display 340 and servers 238 perform the tasks discussed above relative to the processor 115 though these processors may and often perform additional tasks related to medical information, some examples of which are presented and discussed below and the rest of which are contemplated and achieve the various advantages, results and functions presented herein.

The processor 115, in some embodiments, includes display and visualization 340 executing on one or more servers 238, which may be any suitable computing engine, similar to the servers 232, including but not limited to PCs or servers. The display 340 is used to construct presentation and display information to users, such as the patient's records, billing information, and other types of medical information. The display 340, in some embodiments, also performs processing of some of the functions of the processor 115.

As shown in FIG. 3, the servers 232 are coupled to the module 236 and the servers 234, and to the display 340 and the servers 238 and the module 236 and servers 232 are coupled to the display 340 and the servers 238.

In some embodiments, the interface 113, servers 232, module 236, servers 234, display 340, and servers 238 are remotely located relative to the sources 114 and in some embodiments, remotely located relative to one another. Further, they are considered a part of the Internet cloud where, performing their tasks in a manner known as "cloud-computing". However, other manner of achieving the functions and advantages of the invention, including various other of implementation, not shown in FIG. 3 or other figures herein and/or not discussed are contemplated.

Figure 4:
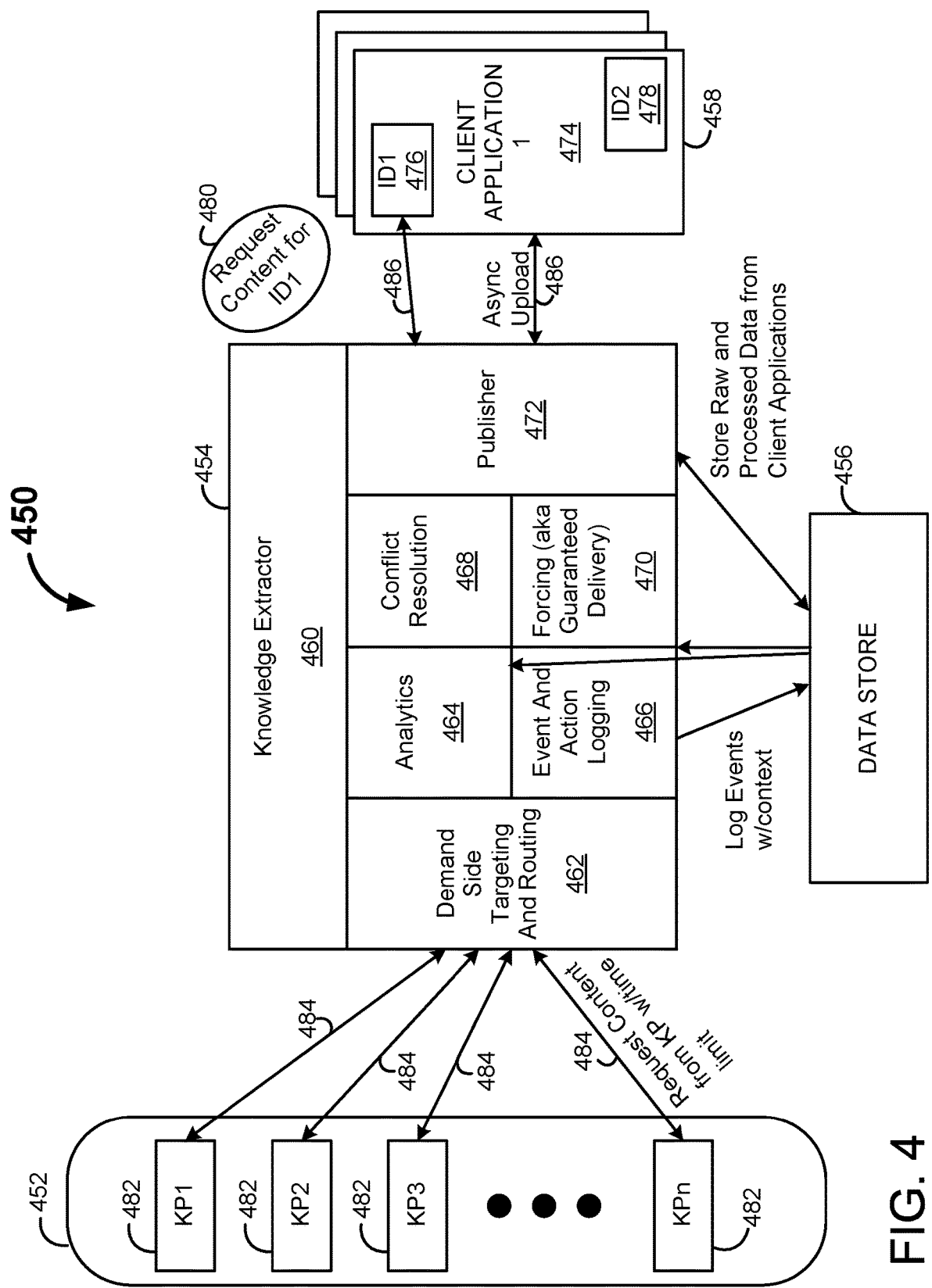
FIG. 4 shows a block diagram of a knowledge extraction system, in accordance with some embodiments.

FIG. 4 shows a block diagram of a knowledge extraction system 450, in accordance with an embodiment of the invention. The knowledge extraction system may be functionally separate from the MINE 112, or may be an integrated feature of the MINE 112, hosted by one or more of the processors 116. Critical to knowledge extraction is the ability to accurately perform text recognition in images of the medical records.

The system 450 is shown to include a knowledge provider block 452, a knowledge extraction and exchange unit 454, a data store block 456, and a client application block 458. The block 458 executes client or user applications 474 using output generated by the knowledge extractor 460.

The block 452 is analogous to the sources 114 of FIG. 1 and is shown to include a number of knowledge providers 482, with each knowledge provider being analogous to one of the sources discussed above relative to the sources 114. The knowledge extraction and exchange unit 454 may include the back-end medical processor, shown in FIGS. 1 and 2. The knowledge extraction and exchange unit 454 is shown to include a demand-side targeting and routing block 462, an analytics block 464, an event and action logging block 466, a conflict resolution block 468, a forcing (or guaranteed delivery) block 470, a publisher block 472, and a knowledge extraction block 460. The block 458 is shown to include one or more impression domain (ID) blocks 476 and 478. While two ID blocks are shown in FIG. 4, it is understood that any number of ID blocks (e.g. problems, procedures, medications, allergies, "did you know?", patient safety items, billing enhancement items, and the like), as required by a user of the system 450, may be employed.

The knowledge extraction and exchange block 454 generally manages the overall process of delivering "content" to the ID blocks 476 and 478, including managing the data store block 456, managing interactions with the knowledge providers 482 and determining which results to present to the client application block 458 (which is generally analogous to the front end processor 115 of FIGS. 1 and 2) when a request of "content" is made by one of the ID blocks 476 and 478 and how to rank the requested results. An example of a request is shown at 480 in FIG. 4 where the block 476 is making the request. "Content", as used herein, refers to any information pertinent to the ID, for example a query string, image or hyperlink.

The data store block 456 is generally a storage device or a database storing raw and processed data received from the block 474, through the unit 454. Raw data is data that comes directly from the application 474. Processed data is data that has been processed or optimized for efficient use by knowledge providers. The knowledge extraction and exchange block 454 causes actions to be logged with context into the data store block 456 when data is being stored therein.

The knowledge extraction and exchange block 454 communicates with the client application block 458 bi-directionally and typically asynchronously such that when there is a change to the underlying data in the application of the block 458, such as an update to the patient chart, the block 458 sends this updated data to the publisher block 472. The client application block 458 is a client or user application with each of its ID blocks querying for and displaying its particular impression domain content. By way of example only, impression domain content includes items such as problems, procedures, medications, allergies, "did you know?", patient safety items, billing enhancement items, and so on. Each ID presents information to the user that is relevant to the specific patient/user/context at the time the information is displayed. For example, a patient safety ID would present a patient's past history of myocardial infarction to a primary care provider if that event were not noted as structured data the user's EHR application. The publisher block 472 receives content requests from the ID blocks 476 and 478 and in response returns content to be displayed in the blocks 476 and 478. Further, the block 472 receives actions (such as clicks) from the ID blocks 476 and 478, receives raw data (such as patient chart updates) from the application block 474, and manages storage of data in the data store block 456 (including action logs, raw client application data, and data extracted for the specific needs of the knowledge providers 482 of the block 452).

The demand side targeting and routing block 462 routes content requests to the different knowledge providers 482, received from the client application block 458 by selecting a subset of knowledge providers in real time which it considers most relevant to the current patient/user/context based on criteria provided by the knowledge provider, such as "patient covered by Medicare Advantage", "user is a cardiologist", or "query includes the term EKG", and subsequently receives their responses, through the knowledge provider links 484. In some embodiments, if a knowledge provider 482 with an outstanding content request does not respond within a prescribed amount of time, the request is cancelled.

The conflict resolution block 468 receives content from the demand side targeting and routing block 462 and advantageously determines which of the responses from the knowledge providers 482 to pass to the forcing block 470 and in which rank order. The conflict resolution block 468 uses the content from the ID block 476 or 478 (e.g., patient, user, query) along with analytics on the performance of past knowledge provider results to determine which results are most likely to be useful. For example, if an endocrinologist user always clicks on the hemoglobin a1c history after performing a diabetes search, the ID for labs may start automatically displaying the history in response to a diabetes context for that particular user. If enough endocrinologists perform the same action, the ID for labs may start automatically displaying the history for all endocrinologists, whereas such an automatic action might not be performed for general practice users searching for the same diabetic context.

The forcing block 470 receives ranked and selected results from the conflict resolution block 468 and further determines to potentially override the ranking determined by the conflict resolution block 468. For example, if only one result can be displayed in a particular ID block, and it receives a high-value reimbursement result and an important patient safety result, the patient safety result might be given priority over the reimbursement result.

The event and action logging block 466 stores action data, such as click-through actions in the data store block 456, along with context information (ID context, date, time). Action data refers to end user actions, e.g., clicking on a particular content that is displayed for more information or history.

The analytics block 464 computes summary statistics for events and actions and places them in the data store block 456 for use by the conflict block 468. End user statistics like click-through rates and dwell times may also be computed by the analytics block 464.

Each of the ID blocks 476 and 478 sends a request to the knowledge extraction and exchange unit 454 asking for certain kinds of result (text, images, links, diagnosis codes) from the knowledge extraction and exchange unit 454. A typical request includes the number of results desired and the context of the request, such as patient identifier, user identifier (and user role, such as specialty, physician or coder or medical assistant, etc.) and the search query. The ID block 476 or 478 is responsible for determining how the results are presented to the user of the system 450. For example, when an action is taken, such as a click on a search link, the ID block 476 or 478 also submits this information to the action logging block 466.

Each of the knowledge providers 482 computes and returns results that are relevant to a particular ID block request. In some embodiments, the knowledge providers 482 have access to the data store block 456. For example, a knowledge provider might return PubMed articles, up-to-date articles, or best treatment practices that are relevant to the patient/user/context.

II. Medical Record Coding Using Weighted Belief Networks

Now that the broad concept of medical information processing and management has been discussed in considerable detail, attention shall now be focused upon the coding of medical records utilizing belief networks. As noted above, the ability to accurately identify actionable codes within a medical record allows for improved reimbursement, and can reduce the need for time consuming and costly manual review.

Figure 5:
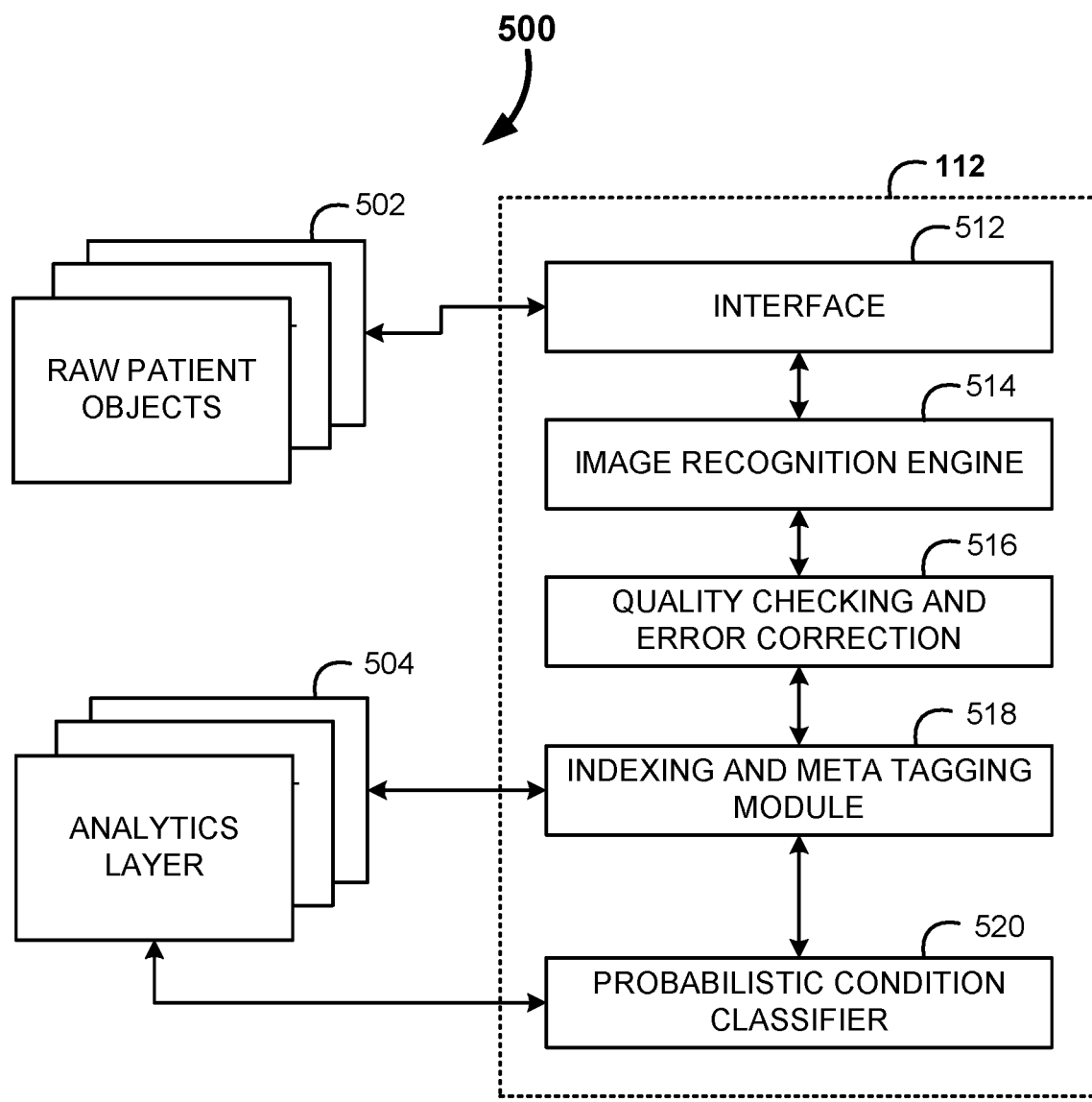
FIG. 5 shows a flow chart of some of the steps performed by the knowledge extractor including probabilistic condition classifier leveraging weighted belief networks, in accordance with some embodiments.

Referring to FIG. 5, a block diagram for one embodiment of the system 500 is illustrated, where the raw data objects 502 are received, processed, and analyzed. The raw data objects 502 may include electronic health records of the many varieties already disclosed. This data is received by an interface 512 of the medical information system 112. As discussed previously, this interface may include any known mechanism for secure data transmission from the data source into the MINE 112.

The records are then subject to optical character recognition (OCR) in order to generate a machine readable dataset in the autofocus OCR engine 514. The machine readable records are then processed by a quality checking and error correction module 516 for de-duplication of records, and other error correction measures. The cleansed data is then processed by an indexing and meta-tagging module 518 to generate indexed and meta-tagged data. Indexing may include parsing the records and identifying concepts using natural language processing (NLP) techniques. The resulting data may be stored within an analytics layer 504 for downstream processes. As already touched upon, these downstream processes may include annotation, search and query, and additional analytics.

Figure 6:
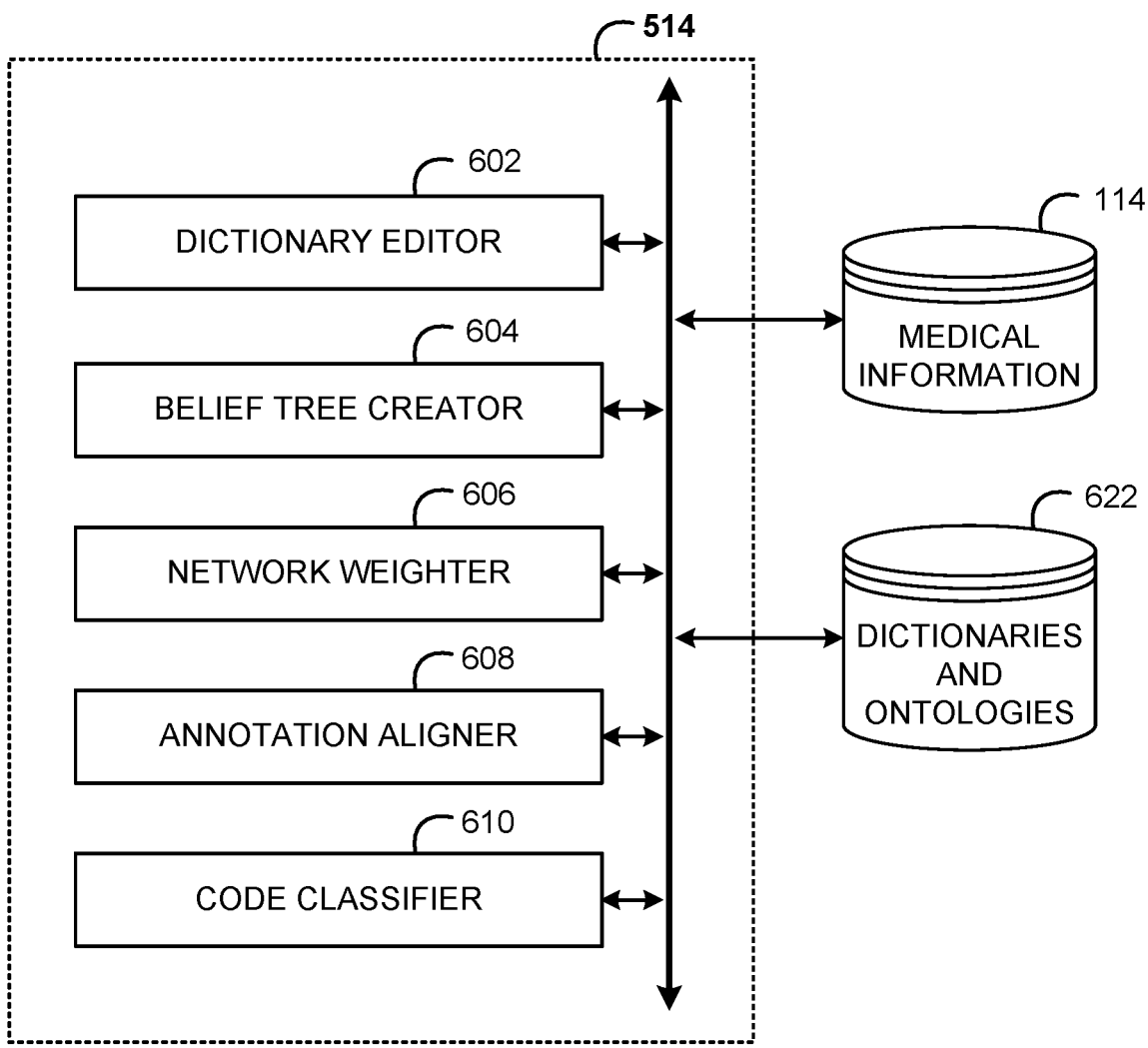
FIG. 6 shows an example of the probabilistic condition classifier, in accordance with some embodiments.

The data in the analytics layer 504 may be leveraged by a probabilistic condition classifier 520 that uses belief networks to generate codes for the indexed and tagged data. FIG. 6 shows a more detailed example of the probabilistic condition classifier 520, in accordance with some embodiments. In this example, the medical information 114 in free-format, including images, as well as the refined indexed and tagged data.

In addition to leveraging the medical information 114, a set of medical indexes, dictionaries and ontologies 622 are utilized in the development and weighting of the belief networks. The dictionaries are generated by a dictionary editor 602, which utilizes public domain data sources for the identification of possible entities. From the dictionary information, the medical records can be analyzed by an entity extractor to determine the entities involved in the given document.

A belief tree creator 604 also utilizes the ontology information 622 to generate a belief tree network for comparing the medical records against. A belief network is a directed model of conditional dependence among a set of random variables, they are also known as Bayesian networks and are acyclic directed graphs which have as nodes random variables (Treatments, Procedures, Medications, Assessments, etc.) and relationships between them codify parent/child relationships.

A network weighter 606 utilizes feedback from medical experts, and statistical analysis of structured and unstructured data that has previously been coded in order to determine the probability (likelihood) that an association is true. Thus a belief network can be described by a directed acyclic graph where each node is labeled by a random variable, a domain for each variable, and a set of conditional probability distributions giving $P(X|parents(X))$ for each variable X. These resulting Bayesian networks are then used to probabilistically classify medical conditions based on evidence asserted in our patient model.

In some embodiments, Web Ontology Language (OWL) is used to construct ontologies to represent concepts and relations associated with patients and their data as provided in the medical records. Categorical concepts are serialized as OWL classes and relationships as either object or data type properties where appropriate. In particular embodiments, OWL constructs are used to restrict instantiation of ontologies and Resource Description Framework (RDF) is used to instantiate them which become queryable through SPARQL (or similar query language) once loaded into a TripleStore (or other database for retrieval of subject-predicate-object triples through semantic queries).

In addition to the belief network being formed, and properly weighted, an annotation aligner 608 may normalize the annotations found in the medical records being reviewed. This may include comparing coder logs to a standardized set of logs (gold standards) and reconciling them. These gold standards may be independently developed by teams of experts, or may be validated through a review of clinical charts, and the condition verified or refuted.

Lastly, the code classifier 610 applies the weighted network to the clinical record to identify the medical condition (or any medical concept). This occurs by identifying any subjects within the triple database, and applies the probability model for the triple to determine if a condition is present.

Figure 7:
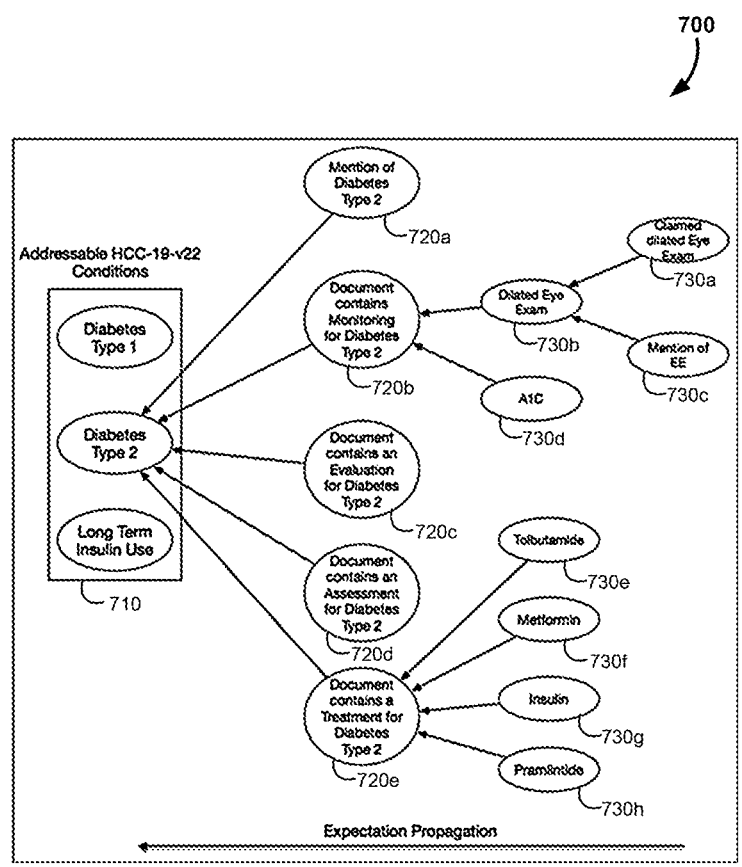
FIG. 7 shows an illustration of an example belief network, in accordance with some embodiments.

Moving on to FIG. 7, an illustration is presented at 700 of one example belief network. This network provides a graphical representation of the relationships between the conditional relations that exist between subjects (treatment elements 730*a-h*) and its corresponding predicate (mentions of diabetes type 2 shown as 720*a-e*) found in the patient medical records. Ultimately this Bayesian network classifies HCC-19 Version 22 (e.g., Diabetes without complications 710), the object of the triple.

This illustrated example belief network is considered unweighted, as there are no probabilistic measures between a subject (metformin 730*f*) for example, and the object (diabetes type 2 710). Prior documents of these connections may be analyzed and modeled for in order to provide a likelihood of the association being true. For example, the system may determine that a mention of the medication 'metformin' is 70% true for the belief that "metformin"—treats—"diabetes type 2". Thus, the mention of metformin is a strong indicator of the disease condition. By compiling the patients' records, these probabilities may reinforce one another, resulting in much higher instances of a particular condition being correct. For example a blood sugar test above a threshold may be associated with diabetes 60% of the time. And the mention of A1C may correspond to a 65% likelihood of diabetes. However these factors combined in a single patient's records may be calculated to be a 98% indicator that the individual has diabetes type 2.

In some embodiments, all potential codes and classifications may be annotated to the medical record for downstream review. In other situations, thresholds may be employed regarding likelihood of a condition in order to cause particular action. For example, in some situations, a potential code if less than 40% likely won't even be mentioned in the annotated record. Between 40-70% likelihood, the medical evidence may be routed to a human coder for review. Between 70-97%, the medical record may be automatically coded as having the condition, and the human coder may be provided the opportunity to approve, but not required to perform a full review of the records. And above 98%, for example, the system may be able to entirely avoid human review, and submit based upon the automated findings.

Figure 8:
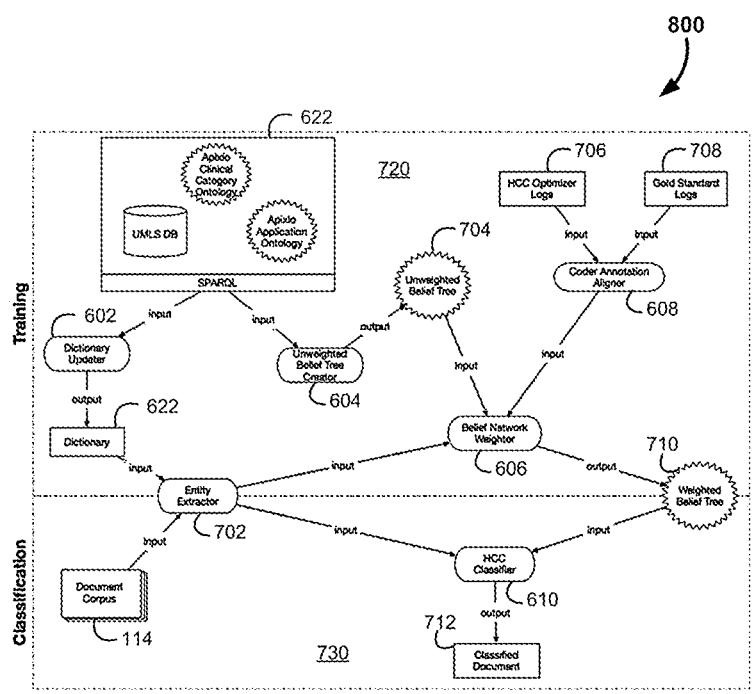
FIG. 8 shows a block diagram of the functional units of the probabilistic condition classifier, in accordance with some embodiments.

Moving to FIG. 8, a block diagram 800 is provided detailing the operation of the probabilistic condition classifier 520, in accordance with some embodiments. In this example, the ontology sources 622 are utilized to generate dictionaries 622 via the dictionary updater/editor 602. Likewise, the conceptual information stored within the ontological structures may be leveraged to design an unweighted belief tree 704 using the unweighted belief tree generator 604.

An entity extractor 702 uses the dictionary 622 on the corpus of medical records 114 to provide entity information to the belief network weighter 606. The belief network weighter 606 also relies upon information regarding frequency of relationships being true that is collected from the coder aligner 608. The coder aligner receives coder optimizer logs 706 and gold standard logs 708 to normalize coder annotations. Using these sources of information, the network weighter 606 is able to assign probabilistic values to the belief network triples (as previously discussed in detail), resulting in a weighted belief network 710.

The activities involved in generating the dictionaries 622, generation of unweighted belief trees 704 and weighting the tree all occur in a training 720 process. Conversely, once the weighted belief tree 710 has been generated, the system can undergo classification processes 730, where the classifier utilizes the corpus of medical records 114 and applies the knowledge in the weighted belief network 710 to generate classified/coded documents 712.

Figure 9:
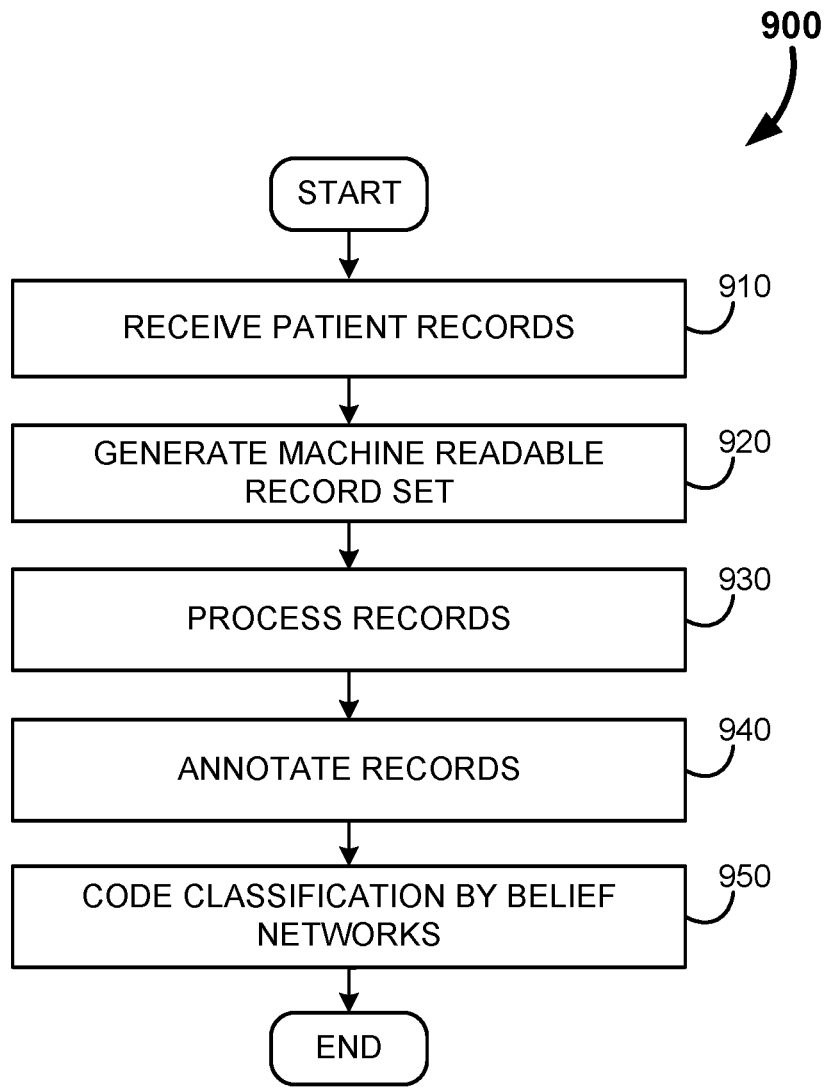
FIG. 9 shows a flow chart of an example method for the coding of medical records using weighted belief networks, in accordance with some embodiments.

FIG. 9 shows a flow chart of an example method 900 for analyzing medical documents for this classification/coding of medical documents, in accordance with some embodiment. In this example process, the patient records are initially received (at 910). The medical records, as previously discussed may take the form of patient charts, records, laboratory results, handwritten notes, radiological images, and the like. These records are subjected to the OCR process in order to generate machine readable documents (at 920). The records are processed (at 930) in order to make them more suited for further downstream analytics.

Figure 10:
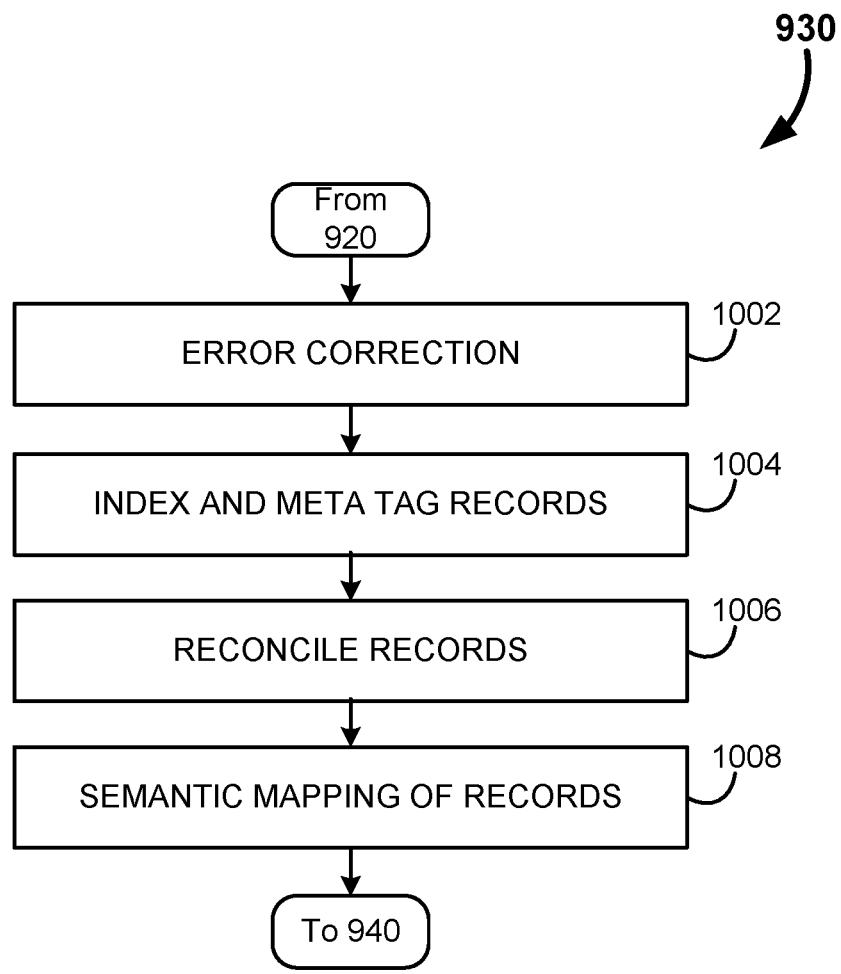
FIG. 10 shows a flow chart of an example method for processing medical documents, in accordance with some embodiments.

FIG. 10 shows one example method for this processing of the medical documents, in accordance with some embodiments. Initially the record processing involves error correction (at 1002). Error correction includes de-duplication of records, removal of records that are believed to not belong within the dataset (for example records that are for someone of the same name, but is otherwise distinguishable from the actual patient), and obviously erroneous records (such as negative numbers or numbers that are outside of the realm of possible).

After error correction, the records may be indexed and meta-tagged (at 1004). Indexing takes processed documents and converts them into formats that make it easy to quickly search across a large collection of documents. Semantic meta-tagging embeds information into the medical information that is relevant thereto and that can be later used to search for certain information for the purpose of reconciliation (at 1006) and search, among many others. Next, the records undergo semantic mapping (at 1008). Semantic mapping may employ known natural language processing techniques, rules based systems, predictive modeling, or any combination thereof. In some embodiments, rule based systems can learn through history, ontology, user-input, the type of user, and a host of other factors, similarities between various information. The system then models the data conceptually by mapping data based on rules for disease/diagnosis relationships, medications, etc. Timing rules may likewise be applied to see how data has changed over time.

Returning to FIG. 9, after the records have been processed, it may be possible for a physician, administrator, agent or other suitable individual to annotate the records (at 940). Record annotation includes the ability to highlight information of particular interest in the records, and/or associate notes with particular regions of the medical records. Not all documents are necessarily annotated. In some embodiments the annotation step may even be omitted. After annotation the resulting records may have codes for which there is evidence in the document classified (at 950) using belief networks.

Figure 11:
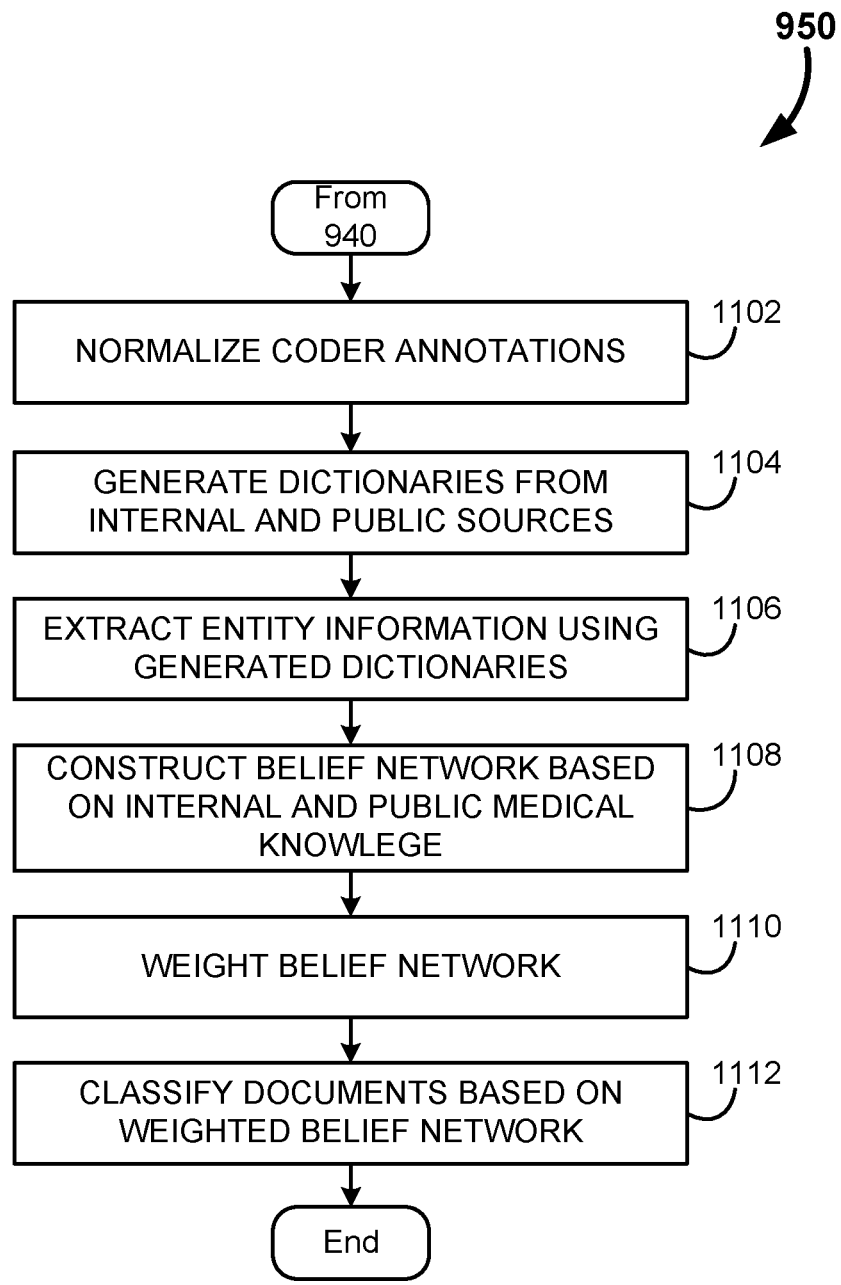
FIG. 11 shows a flow chart of an example method for coding classification, in accordance with some embodiments.

FIG. 11 provides a more detailed description of the process of code classification. As previously touched upon, the annotations are first normalized (at 1102) by the annotation aligner. This normalization may include taking the annotations and comparing them against gold standard annotations, and conforming them accordingly. Alternatively, this normalization efforts may include presenting the annotations to a control team that reviews the annotations and verifies if the associations made within the medical record are accurate or not. Conversely, the annotation normalization may take the form of a team of specialized coders who review documents and make yes/no determinations for conditions based upon evidence within the records. In some cases, this yes/no decision is formatted as a triple (subject-predicate-object) to help facilitate the probability modeling of conditions.

Additionally, dictionaries of entities are generated from public sources (at 1104). The entity information is utilized to identify keywords within the medical records that are associated with a condition or other code-able event (at 1106).

Ontological information, and known medical knowledge from experts are leveraged to generate highly complex belief networks (at 1108). In some embodiments, these belief networks include a triple structure, as previously discussed. The probability modeling that any particular belief string is true is then utilized to weight the belief network (at 1110). The probability modeling is obtained via statistical analysis of verified medical records, such as the normalized annotations generated previously.

The current medical documents are then parsed for entity information, which is compared to the weighted belief network, in order to determine the likelihood of any particular condition or code-able event being present (at 1112). In some embodiments, these code classifications are used to 'pre-classify' the medical records before being sent to a human operator in order to improve workflow throughput and efficiencies. In other circumstances, if the probabilities of the code are high enough, the medical record could even be coded without the need for any human intervention.

After classification, the medical records may be output for additional downstream analysis and consumption by subsequent applications. For example, records may be utilized by statistical research systems, into a coder marketplace or similar coder distribution system, or even directly to a billing application. The indexed records may be made available in a research exchange, or stored for future analytics.

Applications may provide value to the healthcare organization and patients. For example, a quality optimization application may generate actionable care notifications based upon the analyzed records and the classifications. Population analyzers may be a flexible search and query tool that enables the generation of dashboards for risk assessment, performance, compliance, utilization disease registry, and referral management. A HCC optimizer may improve condition capture and risk assessment. It may also monitor coder quality and effort to improve revenue forecasting and reimbursements.

III. System Embodiments

Figure 12A:
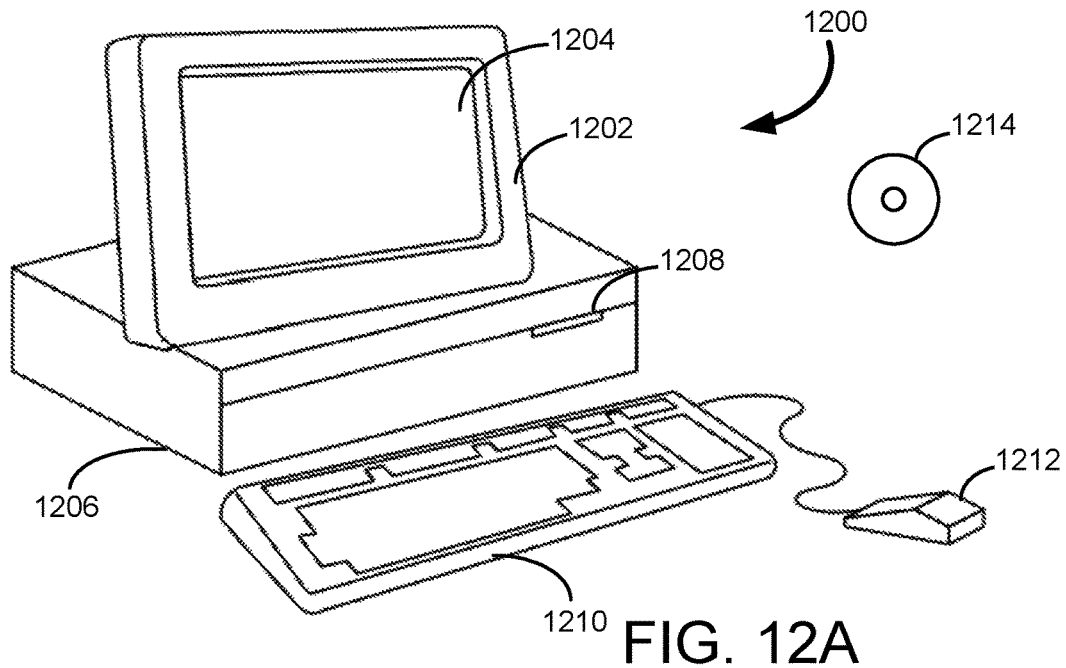
FIGS. 12A and 12B are example computer systems capable of implementing the system for the coding of medical records using weighted belief networks, in accordance with some embodiments.
Figure 12B:
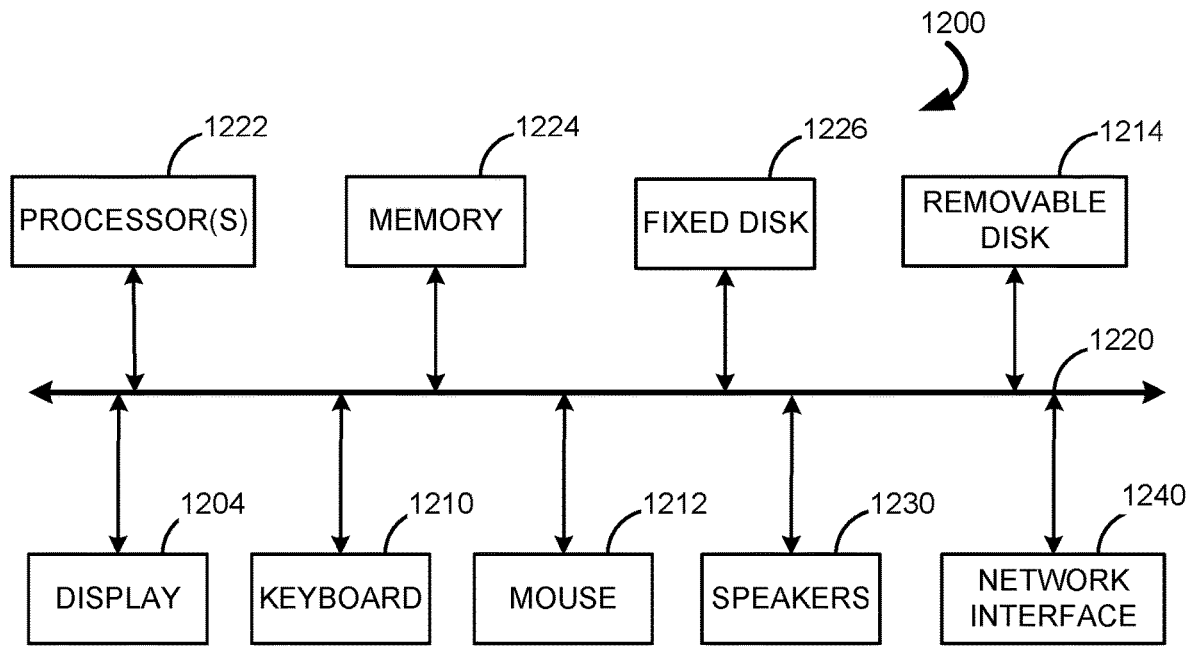

Now that the systems and methods for the coding of medical records using weighted belief networks have been described, attention shall now be focused upon systems capable of executing the above functions. To facilitate this discussion, FIGS. 12A and 12B illustrate a Computer System 1200, which is suitable for implementing embodiments of the present invention. FIG. 12A shows one possible physical form of the Computer System 1200. Of course, the Computer System 1200 may have many physical forms ranging from a printed circuit board, an integrated circuit, and a small handheld device up to a huge super computer. Computer system 1200 may include a Monitor 1202, a Display 1204, a Housing 1206, a Disk Drive 1208, a Keyboard 1210, and a Mouse 1212. Disk 1214 is a computer-readable medium used to transfer data to and from Computer System 1200.

FIG. 12B is an example of a block diagram for Computer System 1200. Attached to System Bus 1220 are a wide variety of subsystems. Processor(s) 1222 (also referred to as central processing units, or CPUs) are coupled to storage devices, including Memory 1224. Memory 1224 includes random access memory (RAM) and read-only memory (ROM). As is well known in the art, ROM acts to transfer data and instructions uni-directionally to the CPU and RAM is used typically to transfer data and instructions in a bi-directional manner. Both of these types of memories may include any suitable of the computer-readable media described below. A Fixed Disk 1226 may also be coupled bi-directionally to the Processor 1222; it provides additional data storage capacity and may also include any of the computer-readable media described below. Fixed Disk 1226 may be used to store programs, data, and the like and is typically a secondary storage medium (such as a hard disk) that is slower than primary storage. It will be appreciated that the information retained within Fixed Disk 1226 may, in appropriate cases, be incorporated in standard fashion as virtual memory in Memory 1224. Removable Disk 1214 may take the form of any of the computer-readable media described below.

Processor 1222 is also coupled to a variety of input/output devices, such as Display 1204, Keyboard 1210, Mouse 1212 and Speakers 1230. In general, an input/output device may be any of: video displays, track balls, mice, keyboards, microphones, touch-sensitive displays, transducer card readers, magnetic or paper tape readers, tablets, styluses, voice or handwriting recognizers, biometrics readers, motion sensors, brain wave readers, or other computers. Processor 1222 optionally may be coupled to another computer or telecommunications network using Network Interface 1240. With such a Network Interface 1240, it is contemplated that the Processor 1222 might receive information from the network, or might output information to the network in the course of performing the above-described coding based upon weighted belief networks. Furthermore, method embodiments of the present invention may execute solely upon Processor 1222 or may execute over a network such as the Internet in conjunction with a remote CPU that shares a portion of the processing.

Software is typically stored in the non-volatile memory and/or the drive unit. Indeed, for large programs, it may not even be possible to store the entire program in the memory. Nevertheless, it should be understood that for software to run, if necessary, it is moved to a computer readable location appropriate for processing, and for illustrative purposes, that location is referred to as the memory in this disclosure. Even when software is moved to the memory for execution, the processor will typically make use of hardware registers to store values associated with the software, and local cache that, ideally, serves to speed up execution. As used herein, a software program is assumed to be stored at any known or convenient location (from non-volatile storage to hardware registers) when the software program is referred to as "implemented in a computer-readable medium." A processor is considered to be "configured to execute a program" when at least one value associated with the program is stored in a register readable by the processor.

In operation, the computer system 1200 can be controlled by operating system software that includes a file management system, such as a disk operating system. One example of operating system software with associated file management system software is the family of operating systems known as Windows® from Microsoft Corporation of Redmond, Wash., and their associated file management systems. Another example of operating system software with its associated file management system software is the Linux operating system and its associated file management system. The file management system is typically stored in the non-volatile memory and/or drive unit and causes the processor to execute the various acts required by the operating system to input and output data and to store data in the memory, including storing files on the non-volatile memory and/or drive unit.

Some portions of the detailed description may be presented in terms of algorithms and symbolic representations of operations on data bits within a computer memory. These algorithmic descriptions and representations are the means used by those skilled in the data processing arts to most effectively convey the substance of their work to others skilled in the art. An algorithm is, here and generally, conceived to be a self-consistent sequence of operations leading to a desired result. The operations are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

The algorithms and displays presented herein are not inherently related to any particular computer or other apparatus. Various general purpose systems may be used with programs in accordance with the teachings herein, or it may prove convenient to construct more specialized apparatus to perform the methods of some embodiments. The required structure for a variety of these systems will appear from the description below. In addition, the techniques are not described with reference to any particular programming language, and various embodiments may, thus, be implemented using a variety of programming languages.

In alternative embodiments, the machine operates as a standalone device or may be connected (e.g., networked) to other machines. In a networked deployment, the machine may operate in the capacity of a server or a client machine in a client-server network environment or as a peer machine in a peer-to-peer (or distributed) network environment.

The machine may be a server computer, a client computer, a personal computer (PC), a tablet PC, a laptop computer, a set-top box (STB), a personal digital assistant (PDA), a cellular telephone, an iPhone, a Blackberry, a processor, a telephone, a web appliance, a network router, switch or bridge, or any machine capable of executing a set of instructions (sequential or otherwise) that specify actions to be taken by that machine.

While the machine-readable medium or machine-readable storage medium is shown in an exemplary embodiment to be a single medium, the term "machine-readable medium" and "machine-readable storage medium" should be taken to include a single medium or multiple media (e.g., a centralized or distributed database, and/or associated caches and servers) that store the one or more sets of instructions. The term "machine-readable medium" and "machine-readable storage medium" shall also be taken to include any medium that is capable of storing, encoding or carrying a set of instructions for execution by the machine and that cause the machine to perform any one or more of the methodologies of the presently disclosed technique and innovation.

In general, the routines executed to implement the embodiments of the disclosure may be implemented as part of an operating system or a specific application, component, program, object, module or sequence of instructions referred to as "computer programs." The computer programs typically comprise one or more instructions set at various times in various memory and storage devices in a computer, and when read and executed by one or more processing units or processors in a computer, cause the computer to perform operations to execute elements involving the various aspects of the disclosure.

Moreover, while embodiments have been described in the context of fully functioning computers and computer systems, those skilled in the art will appreciate that the various embodiments are capable of being distributed as a program product in a variety of forms, and that the disclosure applies equally regardless of the particular type of machine or computer-readable media used to actually effect the distribution.

While this invention has been described in terms of several embodiments, there are alterations, modifications, permutations, and substitute equivalents, which fall within the scope of this invention. Although sub-section titles have been provided to aid in the description of the invention, these titles are merely illustrative and are not intended to limit the scope of the present invention.

It should also be noted that there are many alternative ways of implementing the methods and apparatuses of the present invention. It is therefore intended that the following appended claims be interpreted as including all such alterations, modifications, permutations, and substitute equivalents as fall within the true spirit and scope of the present invention.

What is claimed is:

1. A computerized method for coding medical records comprising:
    receiving medical records;
    generating entity dictionaries from public sources;
    generating a belief network based on medical relationships;
    receiving normalized annotations of historical medical records where the historical medical records include structured and unstructured data that has been previously coded;
    calculating a probability that each association between two concepts in the belief network is true based upon the coded historical medical records;
    weighting the belief network using the probabilities; and
    classifying the medical records by comparing entities within the medical records to the weighted belief network, wherein an entity below a first threshold association with a medical concept will not be coded, an entity above the first threshold but below a second threshold association with the medical concept be provided to a human coder for review, and an entity above the second threshold association with the medical concept will be automatically coded.

2. The method of claim 1, wherein the belief network is a Bayesian network.

3. The method of claim 2, wherein the belief network is a cyclic directed graph with nodes of random variables and relationships between the nodes codify parent/child relationships.

4. The method of claim 3, wherein the belief network has a domain for each random variable.

5. The method of claim 4, wherein the belief network includes a set of conditional probability distributions for each variable X given by: P(X|parents(X)).

6. The method of claim 1, wherein the belief network is a triple data structure comprising a subject-predicate-object.

7. The method of claim 1, wherein the medical relationships used to generate the belief network is a Web Ontology Language (OWL) and Resource Description Framework (RDF) ontologies.

8. The method of claim 1, further comprising preprocessing the medical records.

9. The method of claim 8, wherein the pre-processing includes deduplication of records, indexing the records, meta-tagging the records, and annotating the records.

10. The method of claim 1, further comprising outputting the classified medical records to at least one coder for review.

11. A computerized system for coding medical records comprising:
  an interface for receiving medical records;
  two or more servers;
  wherein the two or more servers comprise at least a hardware processor, and wherein the two or more servers are configured for:
    generating entity dictionaries from public sources;
    generating a belief network based on medical relationships,
    receiving normalized annotations of historical medical records where the historical medical records include structured and unstructured data that has been previously coded,
    calculating a probability that each association between two concepts in the belief network is true based upon the coded historical medical records,
    weighting the belief network using the probabilities, and
    classifying the medical records by comparing entities within the medical records to the weighted belief network, wherein an entity below a first threshold association with a medical concept will not be coded, an entity above the first threshold but below a second threshold association with the medical concept be provided to a human coder for review, and an entity above the second threshold association with the medical concept will be automatically coded.

12. The system of claim 11, wherein the belief network is a Bayesian network.

13. The system of claim 12, wherein the belief network is a cyclic directed graph with nodes of random variables and relationships between the nodes codify parent/child relationships.

14. The system of claim 13, wherein the belief network has a domain for each random variable.

15. The system of claim 14, wherein the belief network includes a set of conditional probability distributions for each variable X given by: $P(X|parents(X))$.

16. The system of claim 11, wherein the belief network is a triple data structure comprising a subject-predicate-object.

17. The system of claim 11, wherein the medical relationships used to generate the belief network is a Web Ontology Language (OWL) and Resource Description Framework (RDF) ontologies.

18. The system of claim 11, wherein one of the two or more servers is further configured for preprocessing the medical records.

19. The system of claim 18, wherein the pre-processing includes deduplication of records, indexing the records, meta-tagging the records, and annotating the records.

20. The system of claim 11, wherein one of the two or more servers is further configured for outputting the classified medical records to at least one coder for review.

* * * * *